(12) United States Patent
Egbaria et al.

(10) Patent No.: US 6,960,563 B2
(45) Date of Patent: Nov. 1, 2005

(54) SPONTANEOUS EMULSIONS CONTAINING CYCLOSPORINE

(75) Inventors: Kamel F. Egbaria, Gurnee, IL (US); Michael J. Groves, Deerfield, IL (US)

(73) Assignee: Morton Grove Pharmaceuticals, Inc., Morton Grove, IL (US)

( * ) Notice: Subject to any disclaimer, the term of this patent is extended or adjusted under 35 U.S.C. 154(b) by 289 days.

(21) Appl. No.: 09/943,687

(22) Filed: Aug. 31, 2001

(65) Prior Publication Data

US 2003/0049280 A1 Mar. 13, 2003

(51) Int. Cl.$^7$ .......................... A61K 38/00; A61K 9/66; C07K 16/00
(52) U.S. Cl. ............................ 514/9; 514/11; 514/937; 514/938; 530/317; 424/451; 424/455; 424/465
(58) Field of Search .................. 514/9, 11, 937, 514/938; 530/317; 424/451, 455, 465

(56) References Cited

U.S. PATENT DOCUMENTS

| | | | |
|---|---|---|---|
| 4,719,239 A | 1/1988 | Muller et al. | 514/785 |
| 4,783,332 A | 11/1988 | Schreuder | 424/59 |
| 4,943,560 A | 7/1990 | Wigness et al. | 514/11 |
| 5,294,604 A | 3/1994 | Nussenblatt et al. | 514/11 |
| 5,504,068 A | 4/1996 | Komiya et al. | 514/11 |
| 5,583,105 A * | 12/1996 | Kovacs et al. | 514/11 |
| 5,639,474 A | 6/1997 | Woo | 424/452 |
| 5,670,478 A | 9/1997 | Stuchlik et al. | 514/11 |
| 5,759,997 A | 6/1998 | Cavanak | 514/11 |
| 5,958,876 A | 9/1999 | Woo | 514/11 |
| 5,962,014 A | 10/1999 | Hauer et al. | 424/450 |
| 5,962,019 A * | 10/1999 | Cho et al. | 424/455 |
| 5,965,160 A | 10/1999 | Benita et al. | 424/455 |
| 5,998,365 A | 12/1999 | Sherman | 514/11 |
| 6,008,192 A | 12/1999 | Al-Razzak et al. | 514/11 |
| 6,063,762 A | 5/2000 | Hong et al. | 514/11 |

FOREIGN PATENT DOCUMENTS

WO    WO99/44584    9/1999

OTHER PUBLICATIONS

General Chemistry, Fifth Edition, Published by HBJ, 1988, p. 460.*

Charman et al., Pharmaceutical Research, vol. 9, No. 1, pp. 87–93, 1992.*

Li et al., S.T.P. Pharma Sciences, vol. 10, No. 4., pp. 341–344, 2000.*

Wakerly et al., "Self–Emulsification of Vegetable Oil—Nonionic Surfactant Mixtures", ACS Symposium Series, 311:242–255, 1986.

Li, Y. and Groves, M., "The Influence of oleic acid on the formation of a spontaneous emulsion," *S.T.P. Pharma Sciences* 10 (4) 341–344 2000.

Craig et al., "An investigation into the effects of drug inclusion on the dielectric response, surface tension and droplet size distribution of self–emulsifying systems," *International Journal of Pharmaceutics*, 96:147–155, 1993.

Shah et al., "Self–emulsifying drug delivery system (SEDDS) with polyglycolyzed glycerides for improving in vitro dissolution and oral absorption of lipophilic drugs," *International Journal of Pharmaceutics*, 106:15–23, 1996.

Charman, et. al., Self–Emulsifying Drug Delivery Systems: Formulation and Biopharmaceutic Evaluation of an Investigational Lipophilic Compound, *Pharmaceutical Research*, vol. 9, No. 1, 1992.

* cited by examiner

*Primary Examiner*—Jon Weber
*Assistant Examiner*—Abdel A. Mohamed

(57) ABSTRACT

A pharmaceutical composition contains cyclosporine as the active ingredient. More specifically, the composition is an orally administered pharmaceutical formulation in the form of a spontaneous emulsion comprising cyclosporine, ethanol ethyl oleate and polyoxyethylene glycerol trioleate. A method for preparing an orally administered pharmaceutical composition involves first dissolving cyclosporine in ethanol. Polyoxyethylene glycerol trioleate and an oil component are then added, mixed and diluted in an aqueous media to form a spontaneous emulsion.

30 Claims, No Drawings

SPONTANEOUS EMULSIONS CONTAINING CYCLOSPORINE

FIELD OF THE INVENTION

The invention relates to pharmaceutical compositions containing cyclosporine as the active ingredient. More specifically, the invention relates to orally administered pharmaceutical compositions in the form of a spontaneous emulsion comprising cyclosporine.

BACKGROUND OF THE INVENTION

Cyclosporines are a group of nonpolar cyclic oligopeptides, which have a broad spectrum of useful pharmacological activities, particularly immuno-suppressive activity and anti-inflammatory activity. The major cyclosporine metabolite is cyclosporine A. Cyclosporine A is a neutral, lipophilic, cyclic endecapeptide with a low aqueous solubility and a molecular weight of 1200 daltons.

Cyclosporine inhibits T cell activation and causes suppression of cell-mediated immune response. Cyclosporine has been used for suppression of immunological responses caused by tissue and organ transplantation, for example, transplantation of the heart, lung, liver, kidney, pancreas, bone marrow, skin and cornea, and especially the transplantation of foreign tissues and organs. In addition, cyclosporine is useful for the suppression of hematological disorders such as anemia, various autoimmune diseases such as systemic lupus erythematosus and idiopathic malabsorption syndrome, and inflammatory diseases such as arthritis and rheumatoid disorders. Cyclosporine is also useful in treatment of protozoal diseases such as malaria and schistosomiasis, and has recently been used in chemotherapy.

Cyclosporine is highly lipophilic and hydrophobic. Therefore, cyclosporine is sparingly soluble in water, and well dissolved in an organic solvent such as methanol, ethanol, acetone, ether, chloroform and the like. Due to the low water-solubility of cyclosporine having the above-mentioned properties, when cyclosporine is administered orally, its bioavailability is extremely low and may be greatly influenced by the conditions of each individual patient. Accordingly, it is very difficult to retain an effective therapeutic concentration. Moreover, cyclosporine may show considerable side effects such as nephrotoxicity. Thus, cyclosporine is very difficult to formulate into a preparation for oral administration due to its low water solubility. Accordingly, numerous studies have been extensively conducted to discover a preparation suitable for the effective oral administration of cyclosporine, which can provide a suitable uniform dosage and appropriate bioavailability.

Previously, the preparations suitable for oral administration of sparingly water-soluble cyclosporine have usually been formulated in the form of an emulsion or microemulsion pre-concentrate (Table 1). Such formulations are commercially available under the names 'Sandimmune' and 'Neoral.' Both formulations are available in solution for oral use or in soft gelatin capsules. The 'Sandimmune' formulation contains cyclosporine in olive oil with the surfactant Labrafil. However, the resulting liquid formulation is administered as an aqueous dilution which makes it very difficult to adapt the subject to its administration and to provide a uniform dosage for oral administration.

The 'Neoral' formulation is a microemulsion pre-concentrate which contains cyclosporine in an anhydrous oily vehicle, medium chain triglycerides, surfactants, glycerol and alcohol.

Another commercially available cyclosporine formulation is marketed under the tradename 'SangCya'. 'SangCya' is a formulation of cyclosporine, the surfactant Tween 80, ethanol, and glycols. Upon dilution, 'SangCya' forms droplet sizes between 200 to 300 nm, which may represent a micellar solution. Recently, however, studies indicate that 'SangCya' has a lower bioavailability upon dilution than other commercially available cyclosporine formulations.

TABLE 1

Comparison of Various Cyclosporine Formulations

| Formulation | Physical State | Droplet Size |
| --- | --- | --- |
| Sandimmune | Precipitate | 2–5 µm |
| Neoral | Microemulsion | 30–50 nm |
| SangCya | Micellar solution | 200–300 nm |

SUMMARY OF THE INVENTION

The present invention provides an orally administered pharmaceutical composition and a method of preparing such composition.

The prevention invention further provides an orally administered pharmaceutical composition comprising cyclosporine, ethanol, polyoxyethylene glycerol trioleate, and an oil component.

The present invention also provides a method of preparing an orally administered pharmaceutical composition. The method involves first dissolving cyclosporine in ethanol. Polyoxyethylene glycerol trioleate and an oil component are then added, mixed and diluted in an aqueous media to form a spontaneous emulsion.

DETAILED DESCRIPTION OF THE INVENTION

The present invention provides a stable cyclosporine composition in the form of a spontaneous emulsion or self-emulsifying drug delivery system (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients.

As emulsion droplet size determines the rate and extent of drug release and absorption, it is considered to be a critical feature for self-emulsification or spontaneous emulsion. Table 1, which compares various cyclosporine formulations, demonstrates the variability in droplet size of different delivery systems. The formulation of the present invention provides a spontaneous emulsion or self-emulsifying delivery system in which the droplets are 50 to 185 nm, preferably from 50 to 150 nm.

Specifically, the present invention provides an orally administered pharmaceutical composition comprising cyclosporine, ethanol, polyoxyethylene glycerol trioleate, and an oil component. The present invention more specifically provides an orally administered pharmaceutical composition comprising cyclosporine, ethanol, polyoxyethylene glycerol trioleate, and ethyl oleate. In addition, the present invention discloses methods for preparing an orally administered pharmaceutical composition.

Cyclosporines are known in the art to exhibit immunosuppressive activity and anti-inflammatory activity. There are a number of cyclosporines available for use in accordance with the present invention. These cyclosporines include Cyclosporine A, Cyclosporine B, Cyclosporine C, Cyclosporine D and Cyclosporine F. The major cyclosporine metabolite, cyclosporine A, is particularly suited for the formulations of the present invention. In the present formulations, cyclosporine A is present at a concentration of from 5 to 20% by weight, preferably from 8 to 12% by weight, and most preferably about 10% by weight.

The formulations of the present invention also comprise an oil component. The chain length, degree of saturation, molecular weight and concentration of the oil influence the final droplet size and polarity in the final emulsion. The oil component may be present in formulations of the present invention at about 40 to about 65 v/v %, more preferably from 55 to 65 v/v %, and most preferably 60 v/v %. In the preferred embodiment, the oil component comprises ethyl oleate.

The solvent used in accordance with the present invention must be non-toxic and be well tolerated physiologically. In addition, the solvent should allow for the incorporation of the pharmaceutically active constituent into solution. The preferred solvent for use in formulations of the present invention is ethanol. Ethanol may be in the form of pure or substantially pure ethanol or a highly concentrated aqueous ethanol solution, such as alcohol USP (95% w/w ethanol), or any other form of ethanol suitable for this use. As used herein, the term "ethanol" shall mean any such form. Ethanol may be present in formulations of the present invention at about 15 to about 40 v/v %, more preferably from 15 to 25 v/v %, and most preferably 20 v/v %.

Also present in the subject formulations is a surfactant, which is polyoxyethylene glycerol trioleate. The surfactant should also be non-toxic and be well tolerated physiologically. The surfactant should be capable of lowering the surface tension of water and stabilizing the oil/water interface after the emulsion is formed. Non-ionic surfactants are more appropriate as they generally have low irritation potential and high chemical stability. The most efficient non-ionic surfactants for the formation of spontaneous emulsions are those with unsaturated acyl chains. These include oleates with HLB values of approximately 11. Polyoxyethylene glycerol trioleate is commercially available under the tradename Tagat TO. Polyoxyethylene glycerol trioleate is present in formulations of the present invention at about 20 to about 50 v/v %.

The preferred formulation of the composition of the present invention comprises cyclosporine, ethanol, polyoxyethylene glycerol trioleate and ethyl oleate in a weight ratio of cyclosporine, pure ethanol, polyoxyethylene glycerol trioleate and ethyl oleate between 5:18:25.9:50.1 to 15:16:23.1:44.9, preferably about 10:17.1:24.5:47.5. The compositions of the present invention upon dilution with an aqueous media at a ratio of 1 part composition to 100 parts aqueous media form a spontaneous emulsion. The spontaneous emulsion is formed as the ethanol is rapidly passed into the aqueous phase, which causes violent perturbation of the oil/water interface and leaves the oil system stranded in the aqueous phase. The oil/water interface develops hexagonal liquid crystals because of the penetration of water molecules into the surfactant and oil/water/interface. Negative interfacial tension forms and disappears rapidly, thereby increasing the violent perturbation along the interface. This results in the formation of smaller oil droplets with hexagonal hydrophilic structures at the interface. The spontaneous emulsion comprises particles having a diameter of 50 to 150 nm.

Compositions of the present invention can be prepared by first dissolving the cyclosporine in ethanol. Polyoxyethylene glycerol trioleate and an oil component are then combined to the cyclosporine/ethanol solution to form a mixture. The mixture is diluted in an aqueous media to allow for the formation of a spontaneous emulsion. In the preferred embodiment, the mixture is diluted 1 part with 100 parts aqueous media. In another preferred embodiment, the diluted mixture is gently mixed to allow dispersion of the droplets formed from the spontaneous emulsion throughout the mixture.

More specifically, a composition in accordance with the present invention and using the constituents in the amounts shown in Table 2 below can be prepared as follows: Cyclosporine, 10 g, is dissolved in 18 g (potable) alcohol USP (95% w/w ethanol) to form a solution. The solution is added with stirring to a mixture of 24.5 g polyoxyethylene glycerol trioleate ('Tagat TO,' Goldschmidt) and 47.5 g ethyl oleate (Croda) to form 100 g of a self-emulsifying mixture. This is generally administered orally as a 1:100 dilution in water or fruit juice.

TABLE 2

| Component | Amount |
|---|---|
| Cyclosporine | 10 g |
| Potable alcohol USP (95% ethanol) | 18 g |
| Polyoxyethylene glycerol trioleate | 24.5 g |
| Ethyl oleate | 47.5 g |

What is claimed is:

1. An orally administered pharmaceutical composition comprising a spontaneous emulsion of cyclosporine, ethanol, polyoxyethylene glycerol trioleate, and an oil component.

2. The pharmaceutical composition of claim 1, wherein said cyclosporine is cyclosporine A.

3. The pharmaceutical composition of claim 1, wherein said oil component is ethyl oleate.

4. The pharmaceutical composition of claim 1, wherein said polyoxyethylene glycerol trioleate is present at about 20 to about 50 v/v %.

5. The pharmaceutical composition of claim 1, wherein said cyclosporine is present at a concentration from about 5 to about 20% by weight.

6. The pharmaceutical composition of claim 5, wherein said cyclosporine is present at a concentration from about 8 to about 12% by weight.

7. The pharmaceutical composition of claim 5, wherein said cyclosporine is present at a concentration of 10% by weight.

8. The pharmaceutical composition of claim 1, wherein said ethanol is present at about 15 to about 40 v/v %.

9. The pharmaceutical composition of claim 8, wherein said ethanol is present at about 15 to about 25 v/v %.

10. The pharmaceutical composition of claim 8, wherein said ethanol is present at 20 v/v %.

11. The pharmaceutical composition of claim 1, wherein said oil component is present at about 40 to about 65 v/v %.

12. The pharmaceutical composition of claim 11, wherein said oil component is present at about 55 to about 65 v/v %.

13. The pharmaceutical composition of claim 11, wherein said oil component is present at 60 v/v %.

14. An orally administered pharmaceutical composition comprising a spontaneous emulsion of cyclosporine, ethanol, polyoxyethylene glycerol trioleate and ethyl oleate In a weight ratio of cyclosporine, pure ethanol, polyoxyethylene glycerol trioleate and ethyl oleate of about 5:18:25.9:50.1 to about 15:16:23.1:44.9.

15. The pharmaceutical composition of claim 14, wherein the weight ratio of cyclosporine, pure ethanol, polyoxyethylene glycerol trioleate and ethyl oleate is 10:17.1:24.5:47.5.

16. The pharmaceutical composition of claim 15, wherein said composition upon dilution with an aqueous media at a ratio of 1 part composition to 100 parts aqueous media forms a spontaneous emulsion.

17. The pharmaceutical composition of claim 16, wherein said spontaneous emulsion comprises particles having a diameter of 50 to 185 nm.

18. The method of claim 17, wherein said spontaneous emulsion comprises particles having a diameter of 50 to 150 nm.

19. A method of preparing an orally administered pharmaceutical composition comprising the steps of:

dissolving cyclosporine in ethanol to form a solution;

combining polyoxyethylene glycerol trioleate and an oil component with the solution to form a mixture; and diluting the mixture with an aqueous media to allow formation of a spontaneous emulsion.

20. The method of claim 19, further comprising the step of gently mixing the diluted mixture to disperse the emulsion.

21. The method of claim 19 wherein the step of diluting further comprises diluting 1 part of the mixture with 100 parts of aqueous media.

22. The method of claim 19, wherein said oil component is ethyl oleate.

23. The method of claim 19, wherein said cyclosporine is cyclosporine A.

24. The method of claim 19, wherein the cyclosporine is present at a concentration of 10% by weight.

25. The method of claim 19, wherein said ethanol is present at about 15 to about 40 v/v %.

26. The method of claim 19, wherein said polyoxyethylene glycerol trioleate is present at about 20 to about 50 v/v %.

27. The method of claim 19, wherein said oil component is present at about 40 to about 65 v/v %.

28. The method of claim 19, wherein said composition comprises cyclosporine, ethanol, polyoxyethylene glycerol trioleate and ethyl oleate in a weight ratio of cyclosporine, pure ethanol, polyoxyethylene glycerol trioleate and ethyl oleate of 10:17.1:24.5:47.5.

29. The method of claim 28, wherein said spontaneous emulsion comprises particles having a diameter of 50 to 185 nm.

30. The method of claim 29, wherein said spontaneous emulsion comprises particles having a diameter of 50 to 150 nm.

* * * * *